(12) United States Patent
Suzuki et al.

(10) Patent No.: US 9,228,942 B2
(45) Date of Patent: Jan. 5, 2016

(54) TURBIDIMETER

(71) Applicant: HORIBA Advanced Techno, Co., Ltd., Kyoto-shi, Kyoto (JP)

(72) Inventors: Riichiro Suzuki, Kyoto (JP); Hiroko Kizaki, Kyoto (JP); Aki Matsuo, Kyoto (JP); Hiroshi Kanda, Kyoto (JP)

(73) Assignee: HORIBA Advanced Techno, Co., Ltd., Kyoto-shi (JP)

( * ) Notice: Subject to any disclaimer, the term of this patent is extended or adjusted under 35 U.S.C. 154(b) by 0 days.

(21) Appl. No.: 14/159,380

(22) Filed: Jan. 20, 2014

(65) Prior Publication Data

US 2014/0204379 A1    Jul. 24, 2014

(30) Foreign Application Priority Data

Jan. 21, 2013  (JP) .................................. 2013-008667
Sep. 30, 2013  (JP) .................................. 2013-204325

(51) Int. Cl.
*G01N 21/51*  (2006.01)
*G01N 21/53*  (2006.01)

(52) U.S. Cl.
CPC .............. *G01N 21/51* (2013.01); *G01N 21/532* (2013.01)

(58) Field of Classification Search
CPC ... G01N 21/53; G01N 21/51; G01N 15/0205; G01N 15/1459; G01N 21/47
USPC ............................. 356/338, 336–337, 343, 73
See application file for complete search history.

(56) References Cited

U.S. PATENT DOCUMENTS

| | | | | |
|---|---|---|---|---|
| 4,250,394 | A * | 2/1981 | O'Connor ...................... | 250/574 |
| 4,740,709 | A * | 4/1988 | Leighton et al. .............. | 250/573 |
| 5,140,168 | A * | 8/1992 | King .................... | G01N 21/532 |
| | | | | 250/575 |
| 5,331,177 | A * | 7/1994 | Kubisiak ............. | A47L 15/4297 |
| | | | | 250/574 |
| 5,453,832 | A * | 9/1995 | Joyce ............................ | 356/338 |
| 6,937,332 | B2 * | 8/2005 | Engler et al. .................. | 356/338 |
| 7,659,980 | B1 * | 2/2010 | Mitchell et al. ............... | 356/339 |
| 8,760,650 | B2 * | 6/2014 | Palumbo ........................ | 356/338 |
| 2006/0103842 | A1 * | 5/2006 | Tokhtuev et al. ............. | 356/338 |
| 2008/0252879 | A1 * | 10/2008 | Ito et al. .......................... | 356/73 |
| 2011/0242523 | A1 * | 10/2011 | Hall ................................ | 356/51 |
| 2011/0273710 | A1 * | 11/2011 | Dong et al. .................... | 356/338 |

FOREIGN PATENT DOCUMENTS

JP         2010060364 A        3/2010

* cited by examiner

*Primary Examiner* — Tarifur Chowdhury
*Assistant Examiner* — Mohamed K Amara
(74) *Attorney, Agent, or Firm* — Alleman Hall McCoy Russell & Tuttle LLP

(57) ABSTRACT

The present invention is intended to provide a turbidimeter having a simple and sturdy structure which is hard to break and exhibits excellent long-term stability by reducing a number of sealing positions, wherein a cylindrical sensor head forming a measurement space is formed of an optically-transparent material. A side wall of the sensor head has accommodating spaces for accommodating a light source, transmitted light detector, and scattered light detector. An inner surface of the side wall of the sensor head is configured to serve as: an optical window for guiding inspection light to the measurement space; an optical window for guiding transmitted light to the transmitted light detector; and an optical window for guiding scattered light to the scattered light detector.

10 Claims, 10 Drawing Sheets

TURBIDIMETER

TECHNICAL FIELD

The present invention relates to a turbidimeter for measuring turbidity of a liquid sample.

BACKGROUND ART

Among conventional turbidity sensors, there is one which includes: a cylindrical measuring cell for accommodating a liquid sample; a light source; a transmitted light detector and scattered light detector; and a sensor accommodating part for accommodating the light source, transmitted light detector, and scattered light detector, wherein the light source, transmitted light detector, and scattered light detector are provided outside the measuring cell, as disclosed in Patent Literature 1. Both end portions in an axial direction of the measuring cell are fixed to the sensor accommodating part via a sealing member. Then, the light source, transmitted light detector, and scattered light detector are fixed in a space which is formed between the sensor accommodating part and the measuring cell.

Further, the measuring cell includes a first transparent window corresponding to the light source, a second transparent window corresponding to the transmitted light detector and a third transparent window corresponding to the scattered light detector. The first, second, and third transparent windows are formed of a material having an optical transparency. The main body portions other than the first, second, and third transparent windows are formed of a material having a light-shielding property.

However, in this turbidity sensor, since the light source, transmitted light detector, and scattered light detector are accommodated in a space formed between the sensor accommodating part and the measuring cell, the liquid sample infiltrates into the space due to factors such as deterioration of the sealing member in both end portions in the axial direction of the measuring cell, and this results in events such as a failure of the light source, transmitted light detector, and scattered light detector. Moreover, it is necessary to assemble the measuring cell and sensor holding part via the sealing member, and therefore there is also a problem that not only does assembly become complicated, but also the turbidimeter is then easily damaged by an external impact.

Further, since the respective transparent windows and the main body portions other than the respective transparent windows in the measuring cell are composed of different materials, it is necessary to ensure sufficient sealing of these transparent windows and main body portions, and therefore a problem may likely arise that the sealing is degraded during a long period of use. Also, it is necessary that the respective transparent windows are fitted to the main body portion of the measuring cell and sufficient sealing is ensured. Therefore, not only does assembly become complicated, but there is also a concern that the transparent windows may be shifted by an impact from the outside.

CITATION LIST

Patent Literature

Patent Literature 1: JP2010-60364A

SUMMARY OF INVENTION

Technical Problem

Therefore, the present invention has been made to solve the problems at once, and an essential object thereof is to provide a turbidimeter having a simple and sturdy structure which is hard to break and exhibits excellent long-term stability by reducing the number of sealing positions.

Solution to Problem

That is, the turbidimeter according to the present invention includes: a bottomed cylindrical sensor head forming a measurement space for accommodating a sample; a light source for irradiating inspection light to the measurement space; a transmitted light detector for detecting transmitted light passing through the measurement space; and a scattered light detector for detecting scattered light scattered in the measurement space, wherein the sensor head is formed of a material having an optical transparency, a side wall of the sensor head includes accommodating spaces for accommodating the light source, transmitted light detector, and scattered light detector, and an inner surface of the side wall of the sensor head is configured to serve as: an inspection light optical window for guiding the inspection light to the measurement space; a transmitted light optical window for guiding the transmitted light to the transmitted light detector; and a scattered light optical window for guiding the scattered light to the scattered light detector.

With this configuration, since the sensor head forming the measurement space is formed of an optically-transparent material and the accommodating spaces for accommodating the light source and respective detectors are formed in the side wall of the sensor head, the conventional measuring cell and sensor accommodating part can be composed of a single member, and therefore it is possible to have a simple and sturdy structure which is hard to break and the sealing positions can be reduced in number. Further, since the inner surface of the side wall of the sensor head is configured to serve as: the inspection light optical window, transmitted light optical window, and scattered light optical window, the optical windows and the other portions can be configured of a single member, and therefore it is possible to have a simple and sturdy structure which is hard to break and the sealing positions can be reduced in number. Furthermore, the sensor head is formed in a cylindrical shape and it can be made hard for ambient light from outside of the sensor head to be incident to the transmitted light optical window and scattered light optical window. Therefore, measurement accuracy of the turbidimeter using a transmission and scattering method can be improved.

It is preferable that, in the side wall of the sensor head, a light absorbing portion is provided between any two of the light source, the transmitted light detector, and the scattered light detector. With this configuration, since the light absorbing portion absorbs the light passing through the inside of the side wall of the sensor head and light which is reflected light reflected by the inner surface of the side wall, it is possible to inhibit stray light composed of such light from being received by the transmitted light detector or scattered light detector (in particular, the scattered light detector), and an accurate measurement can be obtained. In particular, it is desirable that the light absorbing portion is provided between the light source and the scattered light detector in the side wall of the sensor head.

Further, it is preferable that the light absorbing portion is exposed on the inner surface of the side wall of the sensor head. With this configuration, it is possible to reduce the reflected light generated by hitting the inner surface of the side wall, and it is possible to inhibit the reflected light received by the transmitted light detector or scattered light detector (in particular, scattered light detector), and an accurate measurement can be obtained.

One specific implementation aspect of the light absorbing portion is that it is desirable that the light absorbing portion is formed by embedding a light absorbing member in the side wall of the sensor head, and a thickness of the light absorbing member in a radial direction of the sensor head is smaller than a thickness of the side wall of the sensor head. With this configuration, the light absorbing member can be provided while the side wall of the sensor head is formed to have a continuous shape over the circumferential direction, and therefore rigidity of the sensor head can be ensured to thereby prevent deformation thereof.

It is desirable that the accommodating spaces are formed for respectively corresponding to the light source, transmitted light detector, and scattered light detector, and each of the accommodating spaces is formed along a central axis direction from a bottom wall side in the side wall of the sensor head. At this time, a wall portion (inner wall portion) in a side of the measurement space for forming each of the accommodating spaces becomes an optical window. With this configuration, a relative position of the light source, transmitted light detector, and scattered light detector can be positioned by a relative position of the respective accommodating spaces. Further, by fixing the light source, transmitted light detector, and scattered light detector to the respective accommodating spaces, it is possible to prevent a positional displacement of the light source, transmitted light detector, and scattered light detector. Furthermore, by forming the accommodating spaces for the respective light source, transmitted light detector, and scattered light detector, a thickness of the sensor head can be increased and a mechanical strength of the sensor head can be increased. Moreover, since the respective accommodating spaces are formed along the central axis direction from the bottom wall side in the side wall of the sensor head, it is sufficient to only seal between the outer circumferential surface of the sensor head and a housing (casing) for accommodating arithmetic equipment and the like attached to the sensor head, and it is possible to eliminate a seal structure for making the respective accommodating spaces watertight separately.

It is desirable that, a through-hole is formed in the side wall of the sensor head at a position different from the accommodating spaces. Since the through-hole is formed in the side wall in this manner, it is possible to improve a substitution rate and substitution efficiency of a sample in the measurement space. Further, this through-hole also functions as an air vent hole and a hole for discharging dust.

It is desirable that a single holding member is provided for holding the light source, transmitted light detector, and scattered light detector, and the light source, transmitted light detector, and scattered light detector are accommodated in the accommodating spaces by attaching the holding member to the sensor head. With this configuration, since the light source, transmitted light detector, and scattered light detector are fixed to a common holding member, it is possible to facilitate the assembly of accommodating the light source, transmitted light detector, and scattered light detector to the respective accommodating spaces of the sensor head. Further, by defining a relative positional relationship among the light source, transmitted light detector, and scattered light detector by the holding member, positional adjustment of the relative position can be performed after assembly, and when an impact or vibration is applied to the sensor head from the outside during measurement, it is possible to prevent a positional displacement of the light source, transmitted light detector, and scattered light detector.

It is desirable to provide a cleaning unit for cleaning an inspection light optical window, transmitted light optical window, and scattered light optical window. By cleaning the inspection light optical window, transmitted light optical window, and scattered light optical window with this cleaning unit, it is possible to remove air bubbles adhered to the optical windows or impurities in a measurement sample (such as bacteria or adhesive algae, etc.) and eliminate reduction in light intensities of the inspection light, transmitted light, and scattered light, which enables an accurate measurement. Note that one cleaning unit may be provided for cleaning all of the optical windows, or one cleaning unit may be provided for each respective optical window.

It is desirable that the inner surface of the side wall of the sensor head is formed in a cylindrical shape, and the cleaning unit is configured to be rotated about the central axis of the inner surface of the side wall and has a contacting portion contacting over a predetermined range in the central axis direction of the inner surface of the side wall and the contacting portion is inclined in the circumferential direction about the central axis with respect to the central axis. Since the cleaning unit is intended to rotate about the central axis of the inner surface of the side wall and clean the respective optical windows in this manner and the contacting portion thereof is inclined in the circumferential direction about the central axis with respect to the central axis, the dust raked by rotation of the cleaning unit is moved to a rearward side in a rotation direction of the contacting portion. Thus, the dust can be discharged from the measurement spaces.

It is desirable that the sensor head has a slit formed along the central axis direction for communicating the inner surface and outer surface of the side wall of the sensor head, having a configuration so that dust collected by the cleaning unit is discharged from the slit to the outside with rotation of the cleaning unit. With this configuration, the dust collected by the cleaning unit can be discharged outside the sensor head, and therefore the cleaning ability of the cleaning unit can be maintained.

Here, in the case where the contacting portion of the cleaning unit is configured to extend in a different direction from that of the slit, the cleaning unit can be prevented from fitting to the slit and to thereby seize. Also, even if it would not lead to seizing, the cleaning unit can still be prevented from being worn down by fitting to the slit every rotation and deteriorating the cleaning ability.

It is desirable that the cleaning unit is held by the rotating unit rotating about the central axis of the inner surface of the side wall and the rotating unit is formed to have a cylindrical shape and includes an inspection light passage hole for passing the inspection light, a transmitted light passage hole for passing the transmitted light, and a scattered light passage hole for passing the scattered light. By forming the inspection light passage hole, transmitted light passage hole, and scattered light passage hole in the rotating unit in this manner, the portions other than those passage holes function as a light-shielding plate and stray light can be inhibited from being received by the transmitted light detector and scattered light detector, which enables an accurate measurement.

Advantageous Effects of Invention

According to the present invention configured as described above, since the accommodating spaces for accommodating the light source and respective detectors are formed in the side wall of the sensor head made of an optically-transparent material and the inner surface of the side wall of the sensor head is used as the respective optical windows, the turbidimeter can be made with a simple and sturdy structure which is hard to break and sealing positions can be reduced in number. Therefore, it is possible to provide the turbidimeter which exhibits excellent long-term stability.

DESCRIPTION OF EMBODIMENTS

<First Embodiment>

The following describes the first embodiment of a turbidimeter according to the present invention with reference to the accompanying drawings.

A turbidimeter 100 according to a first embodiment is an immersion (throwing-in) type that measures turbidity or suspended solid concentration (SS concentration) of treated water in a water treatment facility such as, for example, a sewage treatment plant, water purification plant, and the like, or measures turbidity or suspended solid concentration (SS concentration) of muddy water discharged from a construction site. In this turbidimeter 100, a measurement range is 0 to 1000 degrees (formazin, kaolin), 0 to 1000 mg/L (kaolin) and minimum resolution is 0.01 degree, 0.01 mg/L.

Figure 1:
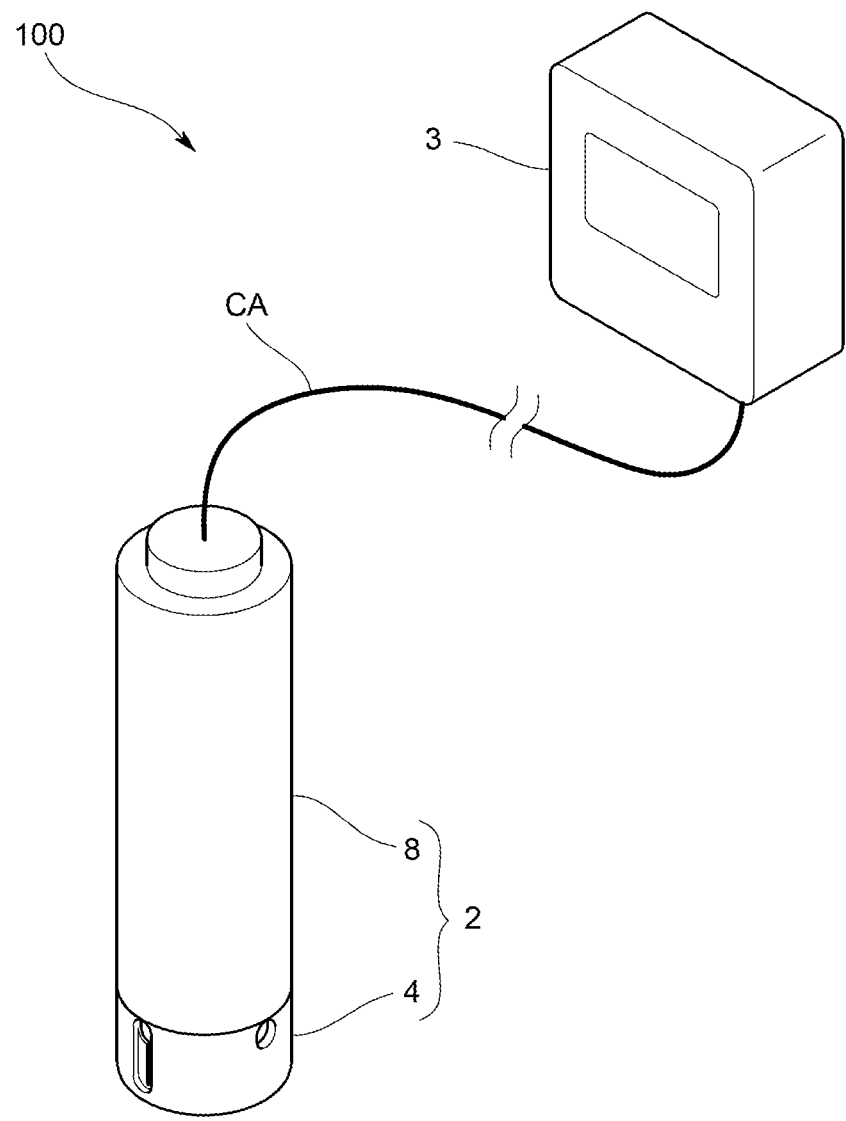
FIG. 1 is a perspective view schematically showing a turbidimeter of the present embodiment.

In specific, as shown in FIG. 1, the turbidimeter 100 includes an immersion type sensor main body 2 and a measuring instrument main body 3 which is electrically connected to the sensor main body 2 via a waterproof electrical cable CA.

Figure 2:
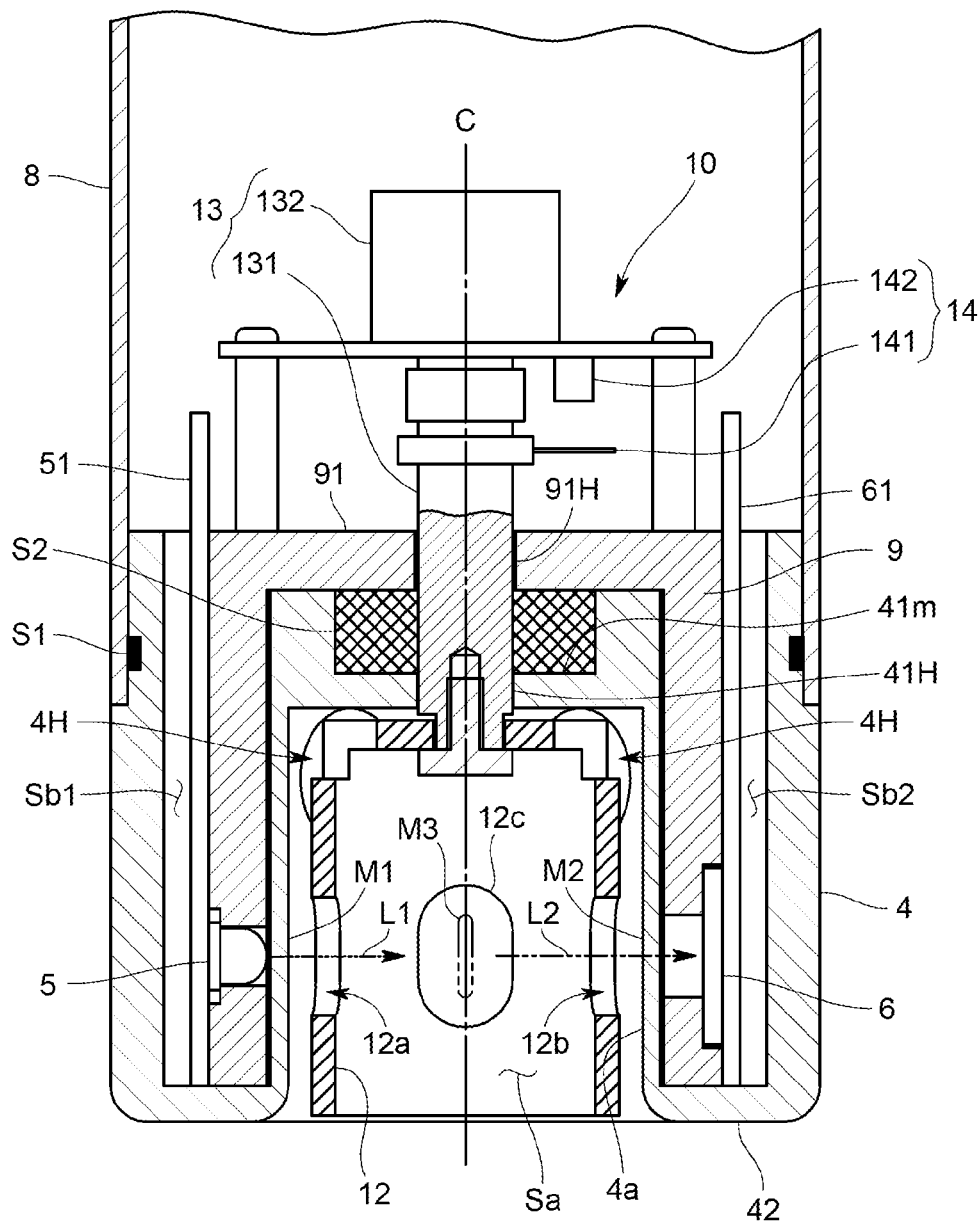
FIG. 2 is a longitudinal sectional view schematically showing a main part of the turbidimeter of the same embodiment.
Figure 3:
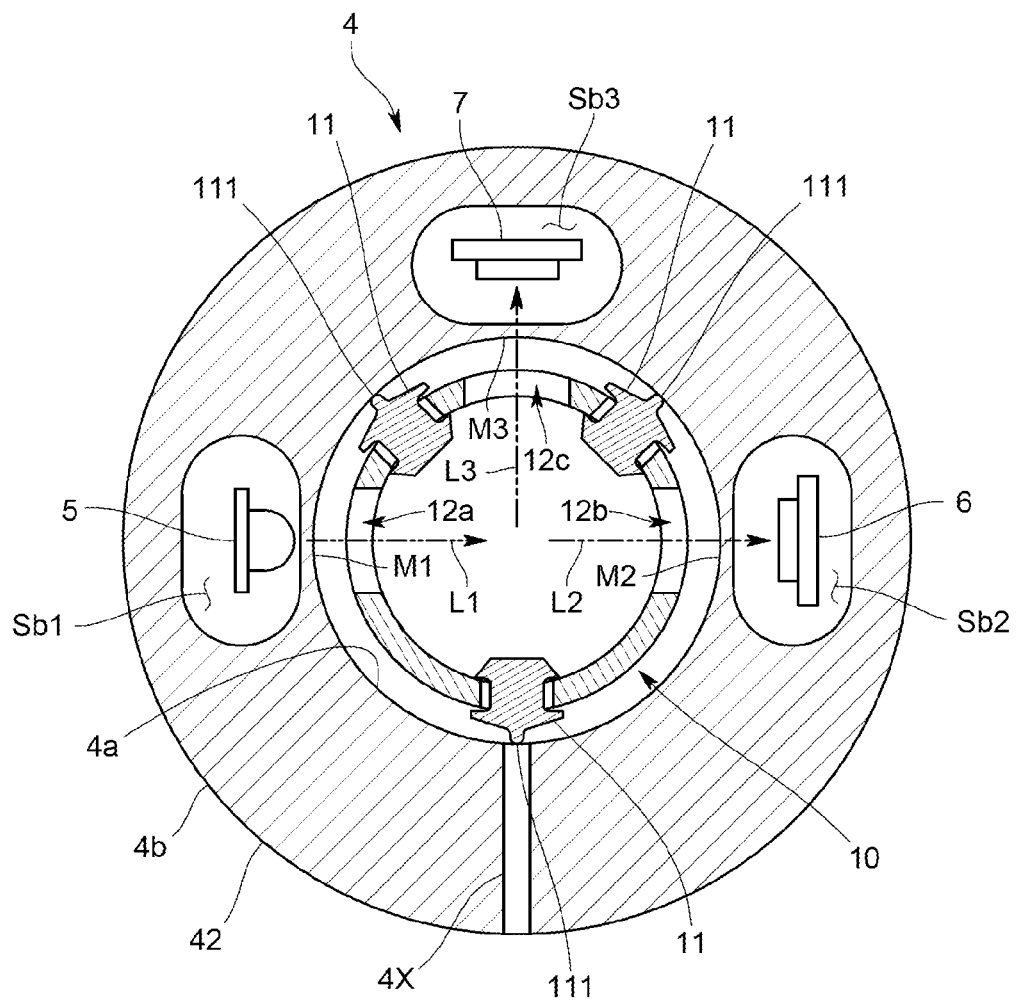
FIG. 3 is a cross-sectional view schematically showing the main part in a measurement position of the same embodiment.

As shown in FIGS. 1 to 3, the sensor main body 2 includes: a closed-bottom cylindrical sensor head 4 having a generally columnar shape and forming a measurement space Sa for accommodating a sample; a light source 5 for irradiating inspection light L1 to the measurement space Sa; a transmitted light detector 6 for detecting transmitted light L2 which has passed through the measurement space Sa; and a scattered light detector 7 for detecting scattered light scattered in the measurement space Sa. The light source 5 is a light-emitting diode (LED) having a peak wavelength, for example, in a near infrared region, and the transmitted light detector 6 and scattered light detector 7 are photodiodes each having a peak sensitivity wavelength which is, for example, in the vicinity of the peak wavelength of the LED. Further, in a side of a bottom wall 41 of the sensor head 4, there is attached a housing 8 for accommodating arithmetic equipment and the like that contains a power supply, an arithmetic part having a memory function unit, and a data logger for recording measurement data and the like of the calculated water quality in time series. It is noted that the sensor head 4 and housing 8 for accommodating arithmetic equipment and the like constitutes a watertight case via a sealing member S1 such as an O-ring.

As shown in FIGS. 2 to 6, the sensor head 4 of the present embodiment is formed to have a closed-bottom, generally cylindrical shape with its one end opened and the other end closed by a bottom wall (upper wall) 41. This sensor head 4 has an inner circumferential surface 4a of a generally circular shape in a cross-section inside thereof and the measurement space Sa is formed by the inner circumferential surface 4a.

Further, the sensor head 4 is integrally molded of a material having optical transparency. Glass, acrylic resin, fluorine resin, silicone resin, or the like material may be used as an example of the material having optical transparency. However, in the present embodiment, there is used a fluorine resin such as PFA (tetrafluoroethylene/perfluoroalkyl vinyl ether copolymer) and the like which excels in optical transparency and stain-resistance. It is noted that this sensor head 4 is integrally formed by cutting a fluorine resin.

Figure 4:
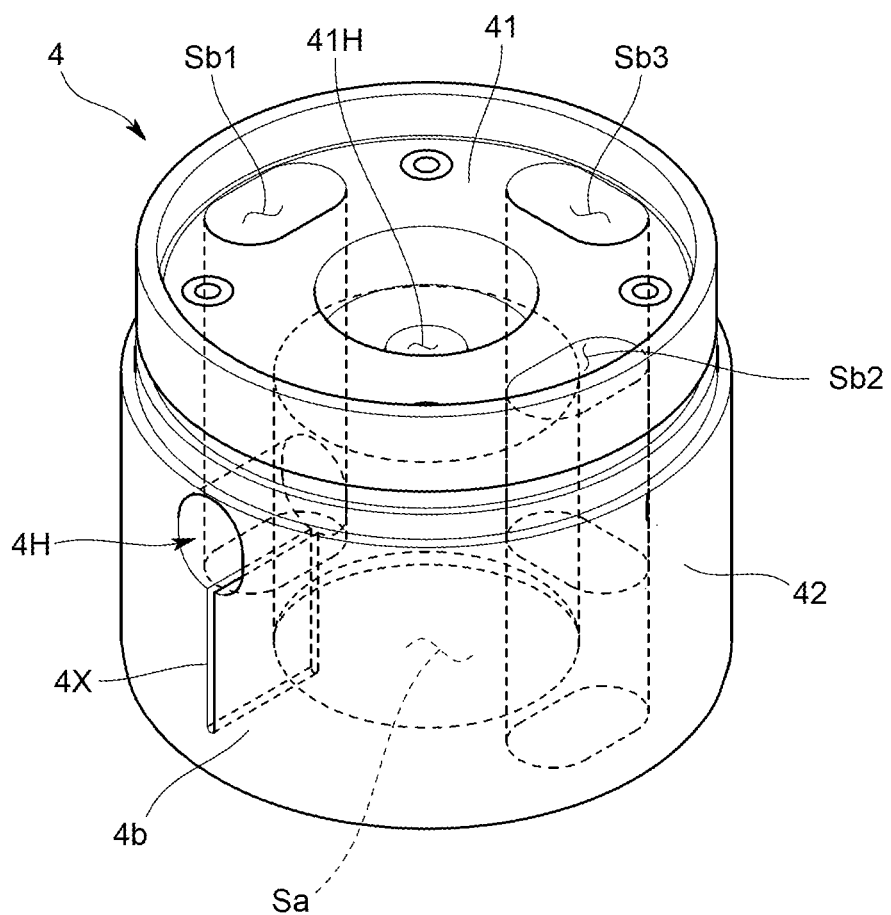
FIG. 4 is a perspective view schematically showing a sensor head of the same embodiment.

In a cylindrical shaped side wall 42 of the sensor head 4, a light source accommodating space Sb1 for accommodating the light source 5, a transmitted light detector accommodating space Sb2 for accommodating the transmitted light detector 6, and a scattered light detector accommodating space Sb3 for accommodating the scattered light detector 7 are formed, especially as shown in FIGS. 3 and 4. These accommodating spaces Sb1 to Sb3 are formed to be extended along a central axis direction from a side of the bottom wall 41 in the side wall 42 of the sensor head 4 (see FIG. 5 and the like).

Figure 6:
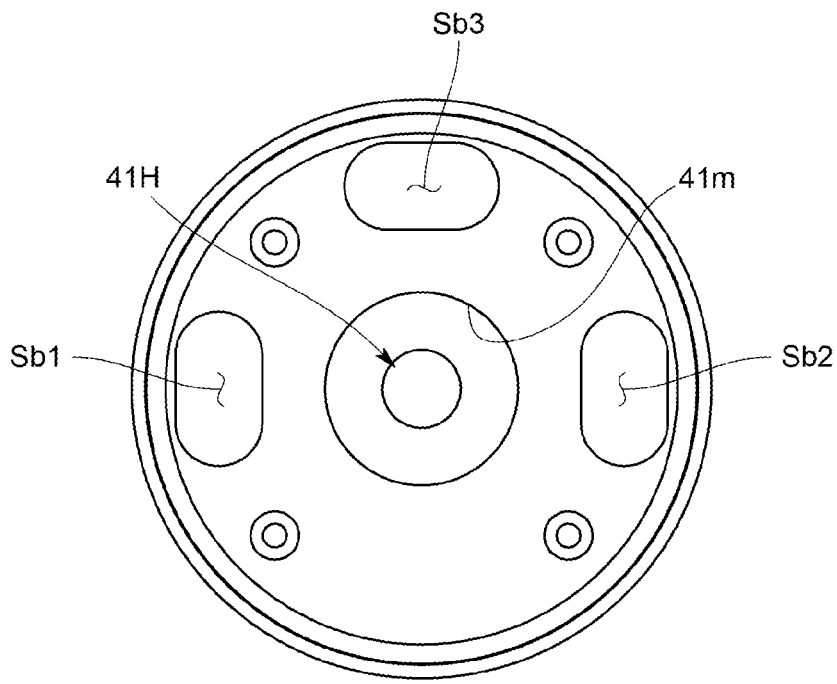
FIG. 6 is a plan view schematically showing the sensor head of the same embodiment.

The light source accommodating space Sb1 and transmitted light detector accommodating space Sb2 are formed to oppose each other across a central axis C and the scattered light detector accommodating space Sb3 is provided in a direction perpendicular to an opposing direction of the light source accommodating space Sb1 and transmitted light detector accommodating space Sb2 (see FIGS. 3 and 6). Thus, each of the accommodating spaces Sb1 to Sb3 is formed in the thickness of the side wall 42 so as to correspond to a positional relationship among the light source 5, transmitted light detector 6, and scattered light detector 7.

Further, especially as shown in FIG. 3, the inner surface of the side wall 42 of the sensor head 4 is configured to serve as an inspection light optical window M1 for guiding inspection light L1 to the measurement space Sa, a transmitted light optical window M2 for guiding transmitted light L2 to the transmitted light detector 6, and a scattered light optical window M3 for guiding scattered light L3 to the scattered light detector 7. In this way, the sensor head 4 is formed by integrally molding the optical windows M1 to M3 and the other portions with a single material.

More specifically, in the side wall 42, a wall portion in a side of the measurement space Sa forming the light source accommodating space Sb1 acts as the inspection light optical window M1, a wall portion in a side of the measurement space Sa forming the transmitted light detector accommodating space Sb2 acts as the transmitted light optical window M2, and a wall portion in a side of the measurement space Sa forming the scattered light detector accommodating space Sb3 acts as the scattered light optical window M3. Thus, in the sensor head 4, the inspection light optical window M1 for guiding the inspection light L1 from the light source 5 to the measurement space Sa and the transmitted light optical window M2 for guiding the transmitted light L2 passed through the measurement space Sa to the transmitted light detector 6 are formed to be opposite from each other. Further, the scattered light optical window M3 for guiding the scattered light L3 scattered in the measurement space Sa to the scattered light detector 7 is formed in a direction perpendicular to the opposing direction of the inspection light optical window M1 and the transmitted light optical window M2.

Figure 5:
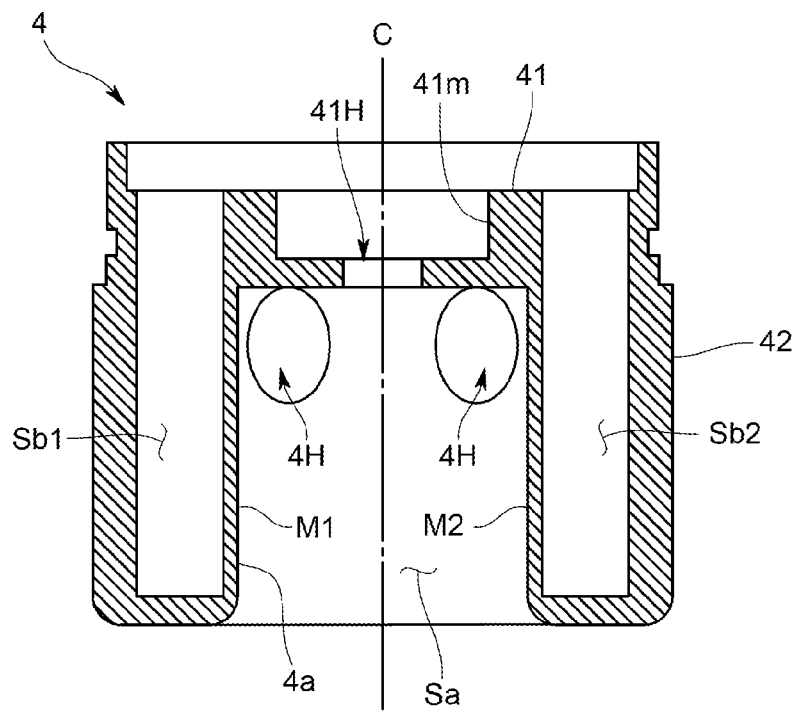
FIG. 5 is a longitudinal sectional view schematically showing the sensor head of the same embodiment.

Further, as shown in FIGS. 4 and 5, one or more throughholes 4H are formed in positions different in the circumferential direction from the accommodating spaces Sb1 to Sb3 in a side of the bottom wall 41 in the side wall 42 of the sensor head 4, i.e., in the bottom surface side of the measurement space Sa in the sensor head 4. This through-hole 4H is intended to penetrate the side wall 42 in the thickness direction and it is intended to not only act as an air vent hole when the sensor head 4 is immersed but also improve a substitution rate and substitution efficiency of a sample in the measurement space Sa. Moreover, it is intended to discharge dust collected by a cleaning unit 11 to be described later.

Figure 7:
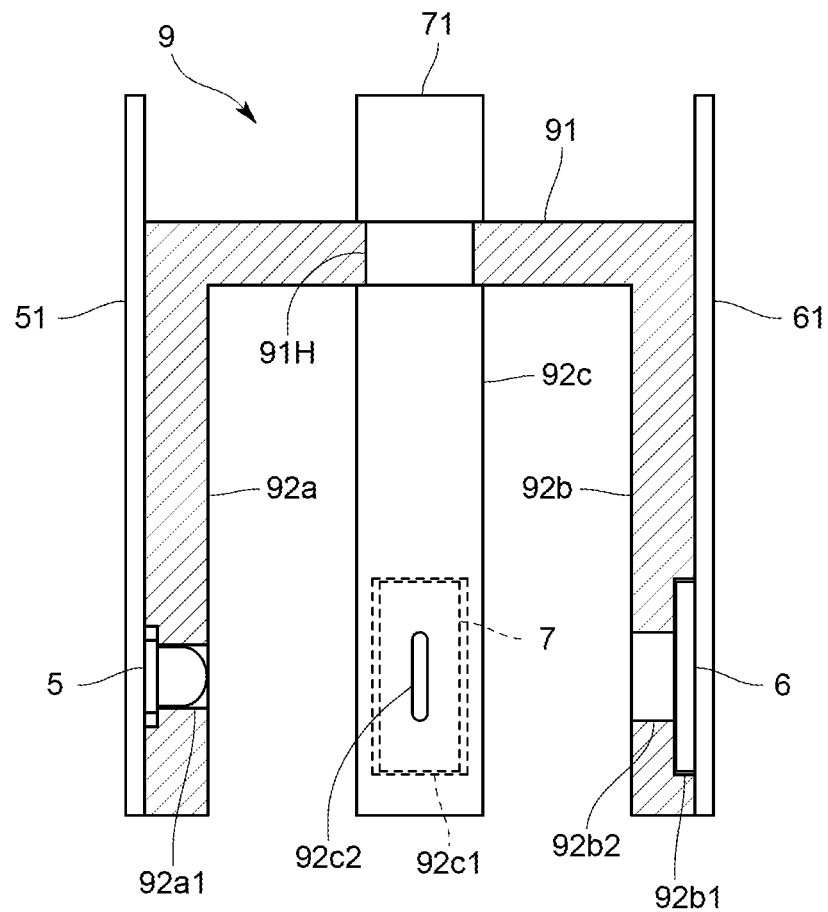
FIG. 7 is a sectional view schematically showing a holding member of the same embodiment.
Figure 8:
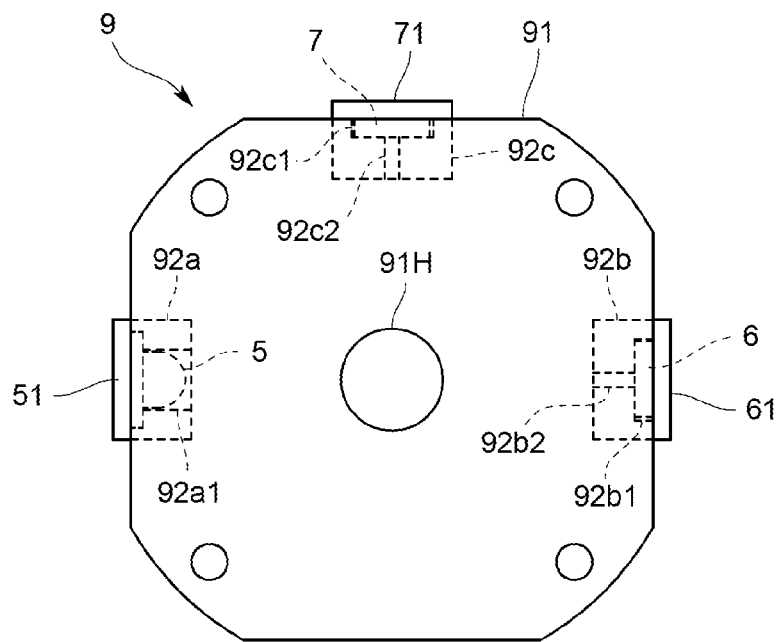
FIG. 8 is a plan view schematically showing the holding member of the same embodiment.

In the sensor head 4 configured in this manner, as shown in FIGS. 2, 7, and 8, the light source 5, transmitted light detector 6, and scattered light detector 7 are held by a single holding member 9 and attached to the sensor head 4.

More specifically, as shown in FIGS. 7 and 8, the holding member 9 includes a fixing plate 91 which is fixed to an upper surface (outer surface) of the bottom wall 41 of the sensor head 4, a light source attachment portion 92a for fixing the light source, a transmitted light detector attachment portion 92b for fixing the transmitted light detector, and a scattered light detector attachment portion 92c for fixing the scattered light detector, wherein these attachment portions 92a, 92b, and 92c are extending downward from the fixing plate 91. These attachment portions 92a, 92b, and 92c are provided in the positions in the fixing plate 91 corresponding to the respective accommodating spaces Sb1 to Sb3 of the sensor head 4. It is noted that there is a through-hole 91H formed in the fixing plate 91, through which a rotation shaft 131 to be described later passes.

An LED substrate 51 including the LED 5 is attached to the light source attachment portion 92a. In the present embodiment, the LED substrate 51 is attached to an outer surface of the light source attachment portion 92a and an accommodating hole 92a1 for accommodating the LED 5 is formed in a portion corresponding to the LED 5. Photodiode substrates 61 and 71 including the photodiodes 6 and 7 are respectively attached to the transmitted light detector attachment portion 92b and scattered light detector attachment portion 92c. In the present embodiment, the photodiode substrates 61 and 71 are attached to the outer surfaces of the respective detector attachment portions 92b and 92c. In the portions corresponding to the photodiodes 6 and 7, accommodating portions 92b1 and 92c1 are formed for accommodating the photodiodes 6 and 7 and also slit holes 92b2 and 92c2 are formed for allowing the transmitted light L2 and scattered light L3, respectively, to pass through. It is noted that both detection signals outputted from the photodiodes 6 and 7 are applied to a calculation part (not shown) accommodated in the housing 8 for accommodating arithmetic equipment and the like.

In this way, since the light source 5, transmitted light detector 6 and scattered light detector 7 are fixed to the single holding member 9, it can be facilitated to attach the light source 5, transmitted light detector 6, and scattered light detector 7 to the respective accommodating spaces Sb1 to Sb3 of the sensor head 4. Further, by defining a relative positional relationship among the light source 5, transmitted light detector 6, and scattered light detector 7 by the holding member 9, positional adjustment after assembly can be performed, and when impact or vibration is applied to the sensor head 4 from the outside during measurement, it is hard to displace the relative positions thereof.

Moreover, in the present embodiment, it is configured so that the attachment portions 92a to 92c are respectively abutted to the inner surfaces forming the accommodating spaces Sb1 to Sb3 and positioned in a state that the fixing plate 91 of the holding member 9 is screwed and fixed to the bottom wall 41 of the sensor head 4. In specific, it is configured so that the inner surfaces and lower surfaces of the attachment portions 92a to 92c are respectively abutted to the inner surfaces and bottom surfaces forming the accommodating spaces Sb1 to Sb3. Since the attachment portions 92a to 92c are respectively abutted to the inner surfaces forming the accommodating spaces Sb1 to Sb3 and positioned in this way, the relative positional displacement of the light source 5, transmitted light detector 6, and scattered light detector 7 can be further reduced. In addition, in the case where the attachment portions 92a to 92c are respectively abutted to only one surface of each of the accommodating spaces Sb1 to Sb3, the positional displacement of the light source 5, transmitted light detector 6, and scattered light detector 7 can be reduced. Here, even in the case where the attachment portions 92a to 92c are respectively pressed against one surface of each of the accommodating spaces Sb1 to Sb3, such an arrangement is still more preferable.

In the present embodiment, as shown in FIGS. 2, 3, 9 and 10, a cleaning mechanism 10 is provided for cleaning the inspection light optical window M1, transmitted light optical window M2, and scattered light optical window M3.

This cleaning mechanism 10 is intended to dispel dirt from the inspection light optical window M1, transmitted light optical window M2, and scattered light optical window M3, and this cleaning mechanism 10 includes: a cleaning unit 11 (see FIGS. 9 and 10) for dispelling dirt and cleaning the inspection light optical window M1, transmitted light optical window M2, and scattered light optical window M3; a rotating unit 12 (see FIGS. 9 and 10) which is installed in the measurement space Sa to hold the cleaning unit 11; a drive unit 13 for rotating the rotating unit 12 within the measurement space Sa; and a position detector 14 for detecting a position of the cleaning unit 11.

The cleaning unit 11 is formed of an elastic member such as rubber, and in the present embodiment, three cleaning units 11 are provided on the outer circumferential surface of the rotating unit 12.

Each cleaning unit 11 is intended to rotate about the central axis C of the inner surface 4a of the side wall 42 in the sensor head 4 and includes a contacting portion 111 contacting over a predetermined range in the direction of the central axis C in the inner surface 4a of the side wall 42. In specific, the contacting portion 111 is formed over a range for sliding over the entirety of each of the optical windows M1 to M3 in the inner surface of the side wall 42 with rotation thereof.

Further, the contacting portion 111 is inclined in a circumferential direction about the central axis C with respect to the central axis C. In the present embodiment, it is inclined in a manner that the upper end of the contacting portion 111 is positioned forward of the lower end in the rotational direction (see FIG. 10)). Since the contacting portion 111 is inclined in this manner, the dust collected by the contacting portion 111 is moved to the lower end of the contacting portion 111 rearward in the rotating direction by rotation of the cleaning unit 11, and the dust is discharged from the measurement space Sa through an opening in the lower end of the sensor head 4.

The rotating unit 12 is made of, for example, black resin having a generally cylindrical shape and the cleaning unit 11 is provided on the outer circumferential surface thereof. In specific, the rotating unit 12 has a closed-bottom cylindrical shape including a side wall portion 121 which faces the inner circumferential surface 4a of the sensor head 4 and a bottom wall portion 122 which is formed in one end side in the axial direction of the side wall portion 121 and faces the bottom wall 41 of the sensor head 4. In the side wall portion 121, an attachment hole 121H is formed for fitting the cleaning unit 11 in an elastically deformed state (see FIG. 9). In the present embodiment, the cleaning unit 11 has an elongated shape extending in the longitudinal direction and the attachment hole 121H is formed to be inclined in the circumferential direction with respect to the central axis C in order that it is provided to be inclined with respect to the central axis C as described above. Thus, by fixing the cleaning unit 11 to the attachment hole 121H of the rotating unit 12, the contacting portion 111 of the cleaning unit 11 is provided and inclined in the circumferential direction with respect to the central axis C.

Especially as shown in FIG. 3, an inspection light passage hole 12a for passing the inspection light L1, a transmitted light passage hole 12b for passing the transmitted light L2, and a scattered light passage hole 12c for passing the scattered light L3 are formed in the side wall portion 121 of the rotating unit 12. These passage holes 12a to 12c are formed so as to respectively face the optical windows M1 to M3, that is, the inspection light passage hole 12a is formed so as to face the inspection light optical window M1 of the sensor head 4, the transmitted light passage hole 12b is formed so as to face the transmitted light optical window M2 of the sensor head 4, and the scattered light passage hole 12c is formed so as to face the scattered light optical window M3 of the sensor head 4, such that the rotating unit 12 is positioned in a measurement position. Thus, since the passage holes 12a to 12c are formed in the side wall portion 121 of the rotating unit 12 so as to respectively face the optical windows M1 to M3, the other portions of the side wall portion 121 function as light shielding plates. Thus, it is possible to inhibit stray light from being received by the transmitted light detector 6 and scattered light detector 7, which allows an accurate measurement to be performed.

Further, in the side wall portion 121 of the rotating unit 12, the three cleaning units 11 are provided so as to position apexes of an isosceles triangle defined by one short side and two long sides, and the cleaning units 11 positioned at the apexes of both ends of the short side are provided so as to interpose the scattered light passage hole 12c therebetween. Thus, in the state that the rotating unit 12 is positioned at the measurement position, the cleaning units 11 positioned at the apexes of both ends of the short side are provided so as to interpose the scattered light optical window M3 therebetween, and therefore an influence of the stray light can be further reduced during measurement of the scattered light, which is easily influenced by the stray light.

Figure 9:
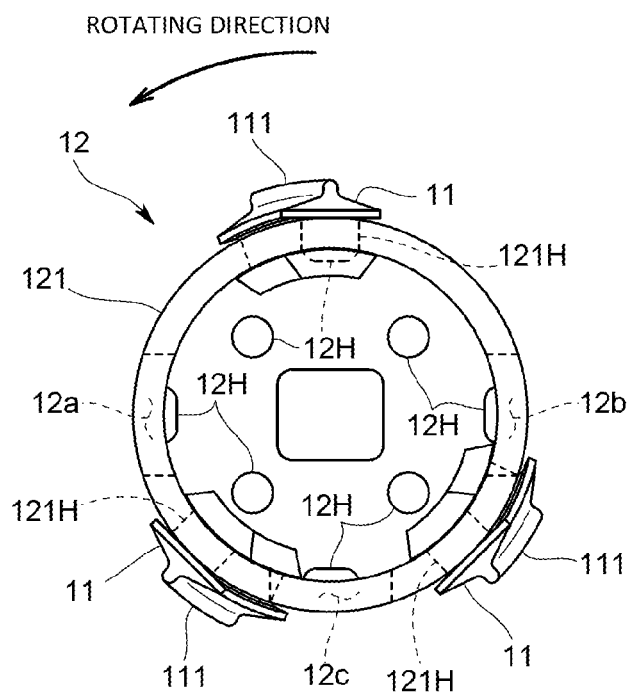
FIG. 9 is a bottom view schematically showing a cleaning unit and rotating unit of the same embodiment.
Figure 10:
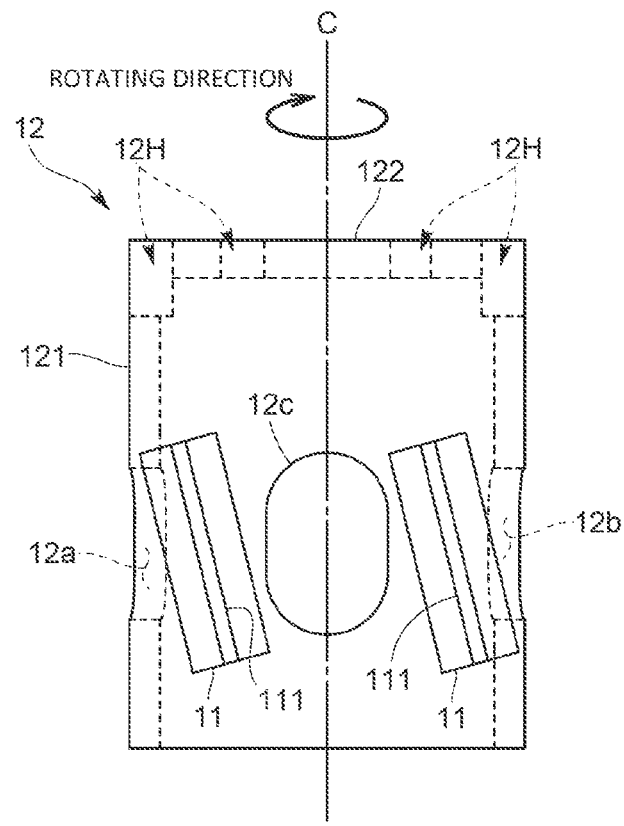
FIG. 10 is a side view schematically showing the cleaning unit and rotating unit of the same embodiment.

Further, through-holes 12H are formed in the bottom wall portion 122 and corner portions between the bottom wall portion 122 and the side wall portion 121 of the rotating unit 12 (see FIGS. 9 and 10). These through-holes 12H are intended to improve a substitution rate and substitution efficiency of a sample in the measurement space Sa. Also, these through-holes 12H function as air vent holes when immersing the sensor head 4.

As shown in FIG. 2, the drive unit 13 is provided for rotating the rotating unit 12 to thereby rotate the cleaning unit 11 about the central axis, and this drive unit 13 includes a rotating shaft 131, one end of which is connected to the rotating unit 12, and a motor 132 such as a stepping motor for rotating the rotating shaft 131. The motor 132 is fixed into a watertight case composed of the sensor head 4 and housing 8 for accommodating arithmetic equipment and the like.

The rotating shaft 131 is provided so as to penetrate a central portion of the bottom wall 41 of the sensor head 4. A shaft seal S2 is provided between the rotating shaft 131 and the through-hole 41H formed in the central portion of the bottom wall 41. This shaft seal S2 is accommodated in a shaft seal accommodating portion 41m (see FIG. 5) formed on the upper surface of the bottom wall 41 of the sensor head 4 to thereby seal between the rotating shaft 131 and the bottom wall 41 of the sensor head 4 in a watertight manner.

As shown in FIG. 2, a position detector 14 is composed of a light reflection sensor 142 which is intended to detect a position of a detection piece 141 provided on the rotating shaft 131 to thereby detect a position of the cleaning unit 11 (rotating unit 12). In specific, the position detector 14 is intended to detect a state that the rotating unit 12 is located in the measurement position, and the detection piece 141 is provided at a position corresponding to the measurement position, and the light reflection sensor 142 detects the detection piece 141 located in the measurement position. Here, the measurement position means a position where the passage holes 12a to 12c of the rotating unit 12 respectively align with the optical windows M1 to M3 of the sensor head 4 (see FIG. 3). Then, immediately after the light reflection sensor 142 detects the detection piece 141, the motor 132 is stopped by a control unit (not shown) several pulses later, for example, in the case where the motor 132 is a stepping motor.

In the cleaning mechanism 10 configured as described above, each of the optical windows M1 to M3 may be automatically cleaned, for example, periodically (for example, every several hours or few days) by the control unit accommodated in the housing 8 for accommodating arithmetic equipment and the like, or it may be also possible that a user is allowed to appropriately perform a cleaning operation using a cleaning key provided in the measuring instrument main body 3.

Further in the present embodiment, as shown in FIGS. 3 and 4, a slit 4X is formed in the side wall 42 of the sensor head 4 along the central axis direction so as to communicate the inner surface 4a with the outer surface 4b of the side wall 42. This slit 4X is a long hole formed in the side wall 42 of the sensor head 4 along the central axis direction and it is communicated with the through-hole 4H in the present embodiment described above. Here, although the slit 4X may be considered to open to the bottom end in the side wall 42 of the sensor head 4, the slit 4X is not open to the bottom end. Rather, the bottom end of the sensor head 4 is structured to be continuous in order to improve the mechanical strength of the sensor head 4.

Figure 11:
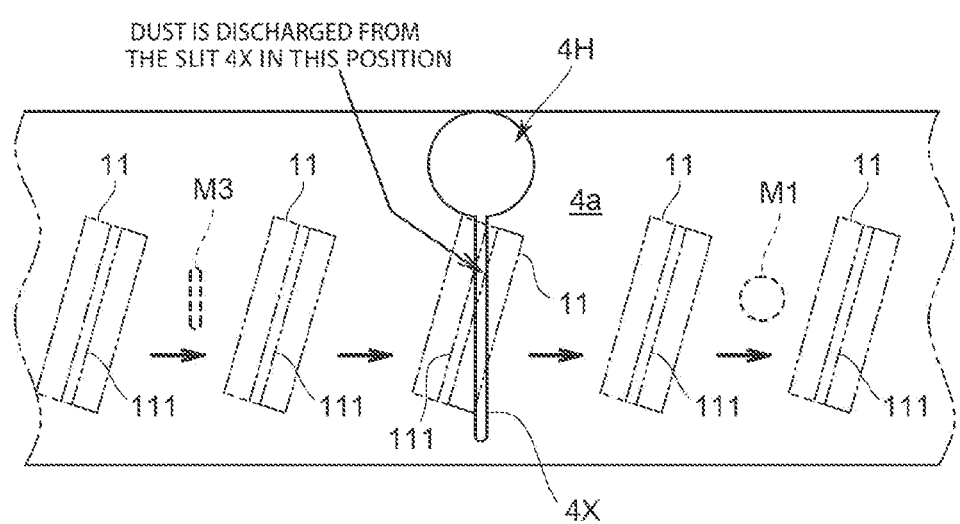
FIG. 11 is a development view schematically showing a movement process of the cleaning unit of the same embodiment.

As shown in FIG. 11, it is configured that the cleaning unit 11 passes through the slit 4X with rotation of the rotating unit 12 and the dust collected by the cleaning unit 11 is discharged from the slit 4X to the outside. By discharging the dust collected by the cleaning unit 11 to the outside from the slit 4X in this way, it is possible to prevent deterioration of cleaning ability of the cleaning unit 11.

In this configuration, whereas the slit 4X extends along the central axis C direction, the direction along which the contacting portion 111 of the cleaning unit 11 extends is inclined in the circumferential direction about the central axis C with respect to the central axis C and the directions along which the slit 4X and the contacting portion 111 of the cleaning unit 11 extend intersect. Therefore, the contacting portion 111 of the cleaning unit 11 can be smoothly rotated without fitting to the slit 4X. Thus, the rotating unit 12 for holding the cleaning unit 11 can be prevented from seizing. Also, even if it does not lead to seizing, the cleaning unit 11 can still be prevented from being easily worn down by fitting to the slit 4X every rotation and deteriorating the cleaning ability.

<Effect of the First Embodiment>

According to the turbidimeter 100 of the first embodiment configured as described above, since the sensor head 4 forming the measurement space Sa is formed of the optically-transparent material and the accommodating spaces Sb1 to Sb3 for accommodating the light source 5 and the respective detectors 6 and 7 are formed in the side wall 42 of the sensor head 4, it is possible to have a simple and sturdy structure which is hard to break and the sealing positions can be reduced in number. Further, since the inner surface 4a of the side wall 42 of the sensor head 4 is configured to serve as: the inspection light optical window M1, transmitted light optical window M2, and scattered light optical window M3, the optical windows M1 to M3 and the other portions can be configured of a single member, and therefore it is possible to have a simple and sturdy structure and the sealing positions can be reduced in number. Furthermore, the sensor head 4 is formed to have a cylindrical shape and it can be made hard for ambient light from outside of the sensor head 4 to be incident to the transmitted light optical window M2 and scattered light optical window M3. Therefore, the measurement accuracy of the turbidimeter 100 using a transmission and scattering method can be improved.

Particularly, in the present embodiment, the sealing portions in the sensor head 4 are only the portion for attaching the housing 8 for accommodating arithmetic equipment and the like in a side of the bottom wall 41 of the sensor head 4 and the portion of the rotating shaft 131 penetrating the bottom wall 41 of the sensor head 4. Therefore, the number of sealing positions can be reduced compared to the conventional turbidimeter.

<Second Embodiment>

Next, the following describes the second embodiment of a turbidimeter according to the present invention with reference to the accompanying drawings. It is noted that, in the embodiment described below, the same reference numerals are assigned to members corresponding to those in the first embodiment.

The turbidimeter 100 according to the second embodiment is mainly different from that of the first embodiment in the configuration of the sensor head 4 and rotating unit 12.

Figure 12:
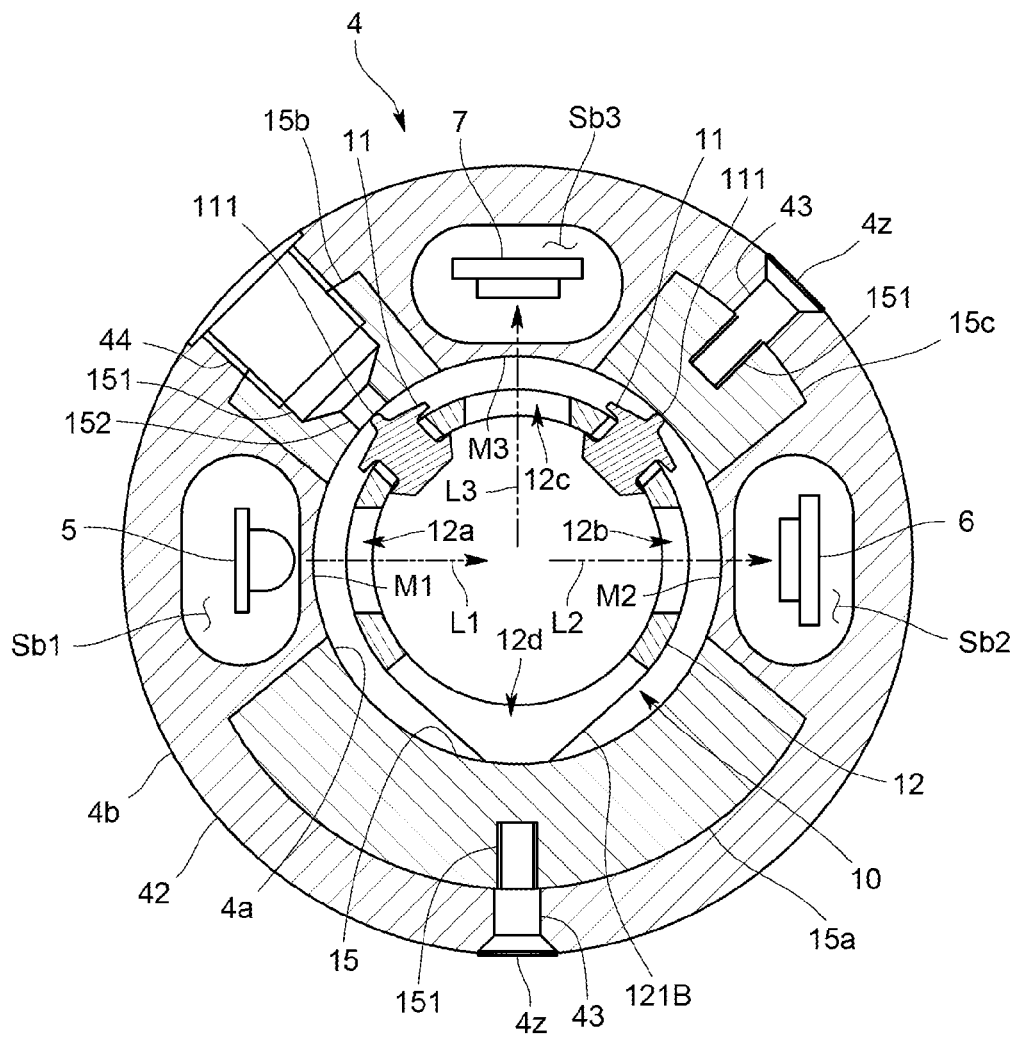
FIG. 12 is a cross-sectional view schematically showing the main part in the measurement position of a modified embodiment.

Regarding the sensor head 4 of the present embodiment, as shown in FIG. 12, in the side wall 42 of the sensor head 4, light absorbing portions 15 are respectively provided between the light source 5 and the transmitted light detector 6, between the light source 5 and the scattered light detector 7, and between the transmitted light detector 6 and the scattered light detector 7.

Specifically, the light absorbing portion 15 is provided so as to expose on the inner surface of the side wall 42 of the sensor head 4, and it is formed by embedding light absorbing members 15a to 15c in the side wall 42 of the sensor head 4.

That is, in the side wall 42 of the sensor head 4, the light absorbing member 15a provided between the light source 5 and the transmitted light detector 6 is embedded so as to expose on the inner surface, the light absorbing member 15b provided between the light source 5 and the scattered light detector 7 is embedded so as to expose on the inner surface, and the light absorbing member 15c provided between the transmitted light detector 6 and the scattered light detector 7 is embedded so as to expose on the inner surface.

Each of the light absorbing members 15a to 15c is formed of a black resin such as, for example, polyphenylene oxide (PPO) and the like. An inner surface of each of the light absorbing members 15a to 15c is formed to have a partial circular shape along the inner circumferential surface of the side wall 42 of the sensor head 4.

Furthermore, the thickness of each of the light absorbing members 15a to 15c in the radial direction of the sensor head 4 is configured to be smaller than the thickness of the side wall 42 of the sensor head 4. That is, an outer diameter portion in the side wall 42 of the sensor head 4 is formed to have a cylindrical shape continuous over the entirety in the circumferential direction and an inner diameter portion thereof in the sensor head 4 is formed to have a shape forming an accommodating recess for accommodating each of the light absorbing members 15a to 15c. Thus, the rigidity of the sensor head 4 is ensured to thereby prevent deformation thereof.

Further, each of the light absorbing members 15a to 15c is secured to the side wall 42 of the sensor head 4 by a screw 4z. Specifically, in order to secure the light absorbing members 15a to 15c to the sensor head 4 by screws 4z, through-holes 43 are formed in the sensor head 4 and screw holes 151 are formed in the light absorbing members 15a to 15c, respectively.

Figure 13:
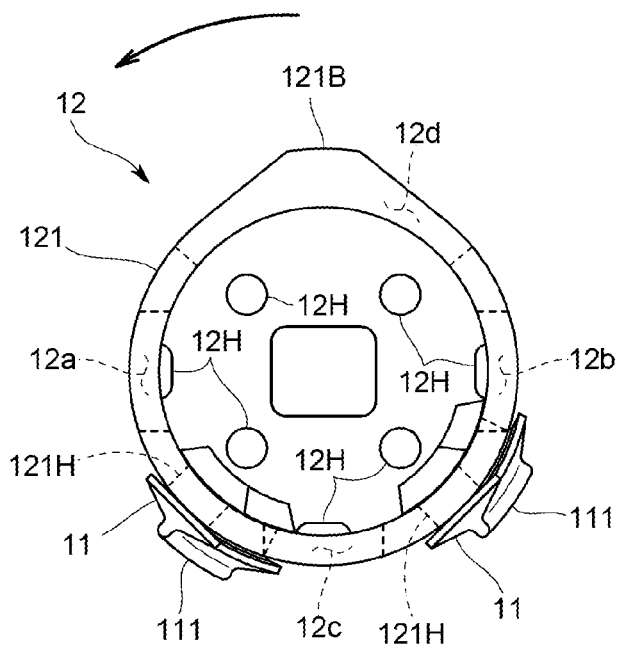
FIG. 13 is a bottom view schematically showing the cleaning unit and rotating unit of the modified embodiment.
Figure 14:
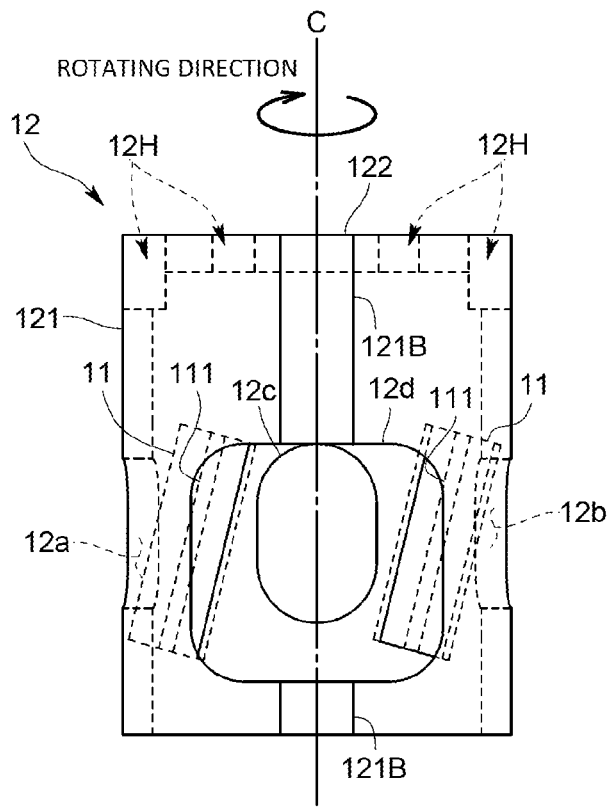
FIG. 14 is a side view schematically showing the cleaning unit and rotating unit of the modified embodiment.

Regarding the rotating unit 12 of the present embodiment, as shown in FIGS. 12 to 14, an antireflective passage hole 12d for passing stray light such as scattered light and the like caused by direct light generated by the light source 5 and scattering thereof is formed between the inspection light passage hole 12a and the transmitted light passage hole 12b in a side wall portion 121 of the rotating unit 12.

This antireflective passage hole 12d is intended to reduce reflected light caused by reflection on the inner surface of the side wall portion 121 of the rotating unit 12 and make it hard for the light to be received by each of the light detectors 6 and 7, and it is provided to be opposed to the scattered light passage hole 12c in the side wall portion 121. Specifically, the antireflective passage hole 12d is formed to have, for example, a generally rectangular shape in a side view and it is configured so that a width of an opening along the circumferential direction is larger than that of the scattered light passage hole 12c. Further, an axial size of the antireflective passage hole 12d in a side view is configured to be larger than that of the scattered light passage hole 12c. Since the antireflective passage hole 12d is formed in the side wall portion 121 of the rotating unit 12 in this way, reception of the reflected light caused by reflection on the inner surface of the side wall portion 121 of the rotating unit 12 by each of the light detectors 6 and 7 can be inhibited. Since the inner surface of the rotating unit 12 is not cleaned by a unit such as the cleaning unit 11 as for the inner surface of the sensor head 4, it is easily stained and reflected light is easily caused by the stains. However, by forming the antireflective passage hole 12d, the reflected light caused by such defects as stains of the inner surface of the rotating unit 12 can be reduced and the stray light reflected by the inner surface of the rotating unit 12 can be prevented from being received by the transmitted light detector 6 and scattered light detector 7, and therefore allowing an accurate measurement to be performed.

And in the turbidimeter 100 of the present embodiment, the antireflective passage hole 12d is formed so as to face the light absorbing member 15a at a measurement position where the passage holes 12a to 12c of the rotating unit 12 respectively align with the optical windows M1 to M3 of the sensor head 4. Specifically, regarding the positional relationship between the antireflective passage hole 12d and the light absorbing member 15a, it is configured in such a manner that only the light absorbing member 15a is visible from the antireflective passage hole 12d when viewing the antireflective passage hole 12d from the intersection between the central axis C and the inspection light L1. Since the antireflective passage hole 12d and the light absorbing member 15a face each other in this way, with the configuration for preventing reflection on the side wall portion 121 of the rotating unit 12 with provision of the antireflective passage hole 12d, the light passing through the antireflective passage hole 12d can be further prevented from being reflected by the inner surface of the side wall 42 of the sensor head 4, and the reflective light caused on the inner surface of the side wall 42 can be prevented from being received by each of the detectors 6 and 7.

Moreover, with formation of the antireflective passage hole 12d in the rotating unit 12, as shown in FIGS. 12 to 14, the rotating unit 12 of the present embodiment is configured to provide two cleaning units 11 across the scattered light passage hole 12c. In this case, in order for the position of the rotating unit 12 to be maintained against a reaction force which is caused by contacting the two cleaning units 11 with the inner surface of the sensor head 4, there is a thick portion 121B which is made thick in the upper and lower direction of the antireflective passage hole 12d in the side wall portion 121 of the rotating unit 12 so as to abut to the inner surface of the side wall 42 of the sensor head 4.

Furthermore, in the present embodiment, as shown in FIG. 12, there is a washing nozzle 44 formed on the side wall 42 and a light absorbing member 15b of the sensor head 4 for washing the inner surface of the side wall 42 of the sensor head 4, cleaning units 11, or rotating unit 12. This washing nozzle 44 is intended to communicate the outside of the sensor head 4 with the measurement space Sa and has a flow path which is reduced in diameter toward the measurement space Sa from the outside of the sensor head 4. Note that, although the washing nozzle 44 is formed on the light absorbing member 15b in FIG. 12, it may be formed on the other light absorbing members 15a and 15c or may be formed on the side wall 42 and not on the light absorbing members 15a to 15c. By forming the washing nozzle 44 in this way, washing liquid such as water can be introduced into the measurement space Sa through the washing nozzle 44 and a through-hole 152. Therefore, the inner surface of the side wall 42 of the sensor head 4, rotating unit 12, or cleaning unit 11 can be easily washed.

<Effect of Second Embodiment>

According to the turbidimeter 100 configured as described above, since the light absorbing portion 15 is provided by embedding the light absorbing members 15a to 15c in the side wall 42 of the sensor head 4, it is possible to absorb light which passes through the inside of the side wall 42 of the sensor head 4 or which becomes reflected light reflected by the inner surface of the side wall 42, and the stray light composed of such light can be prevented from being received by the transmitted light detector 6 and scattered light detector 7 (especially, scattered light detector 7). Thus, accurate measurement can be obtained.

Note that the present invention should not be limited to the above embodiments.

For example, in the above embodiments, although the accommodating spaces Sb1 to Sb3 are formed to respectively correspond to the light source 5, transmitted light detector 6, and scattered light detector 7, it may be possible to form accommodating spaces for accommodating at least two of them at once. By forming the measurement spaces for accommodating at least two of them in this way, the sensor head 4 can be reduced in weight.

Further, in the above embodiments, the contacting portion 111 of the cleaning unit 11 may be inclined so that the lower end thereof is positioned forward of the upper end in the circumferential direction. With this configuration, the collected dust and the like can be discharged through the through-hole 4H formed in the side of the bottom wall 41 of the sensor head 4.

Moreover, the number of the cleaning units 11 should not be limited to each of the above embodiments. For example, in the first embodiment, one or two cleaning units 11 may be provided and four or more cleaning units 11 may be provided. In order to prevent the stray light from being received by the scattered light detector, it is desirable that at least two or more cleaning units are provided.

Furthermore, in the above embodiments, although the light source 5, transmitted light detector 6, and scattered light detector 7 are configured to be held by a single holding member 9 and accommodated in the sensor head 4 at the same time, they may be configured to be separately accommodated in the respective accommodating spaces Sb1 to Sb3 instead of held by a single holding member 9. With this configuration, in the case where any one of the light source 5, transmitted light detector 6, and scattered light detector 7 is substituted, it is not necessary to remove the other two from the sensor head 4 and therefore substitution can be facilitated.

In addition, in the above embodiments, although the cleaning unit 11 is intended to rotate about the central axis C of the inner surface of the side wall 42, the cleaning unit 11 may be configured to move back and forth along the central axis C of the inner surface 4a of the side wall 42.

Furthermore, although the position detector 14 of the above embodiments is intended to detect the detection piece 141 provided on the rotating shaft 131 by the light reflection sensor 142, detection may be using a light intensity signal obtained from the transmitted light detector 6 or scattered light detector 7 when the rotating unit 12 is rotated. For example, in the case where the position is detected using the light intensity signal from the transmitted light detector 6, since the light intensity signal becomes the maximum value at the measurement position, using this maximum value, it can be detected that the rotating unit 12 is positioned at the measurement position.

In addition, in the above embodiments, although the slit 4X extends along the direction of the central axis C and the direction along which the contacting portion 111 of the cleaning unit 11 extends is inclined from the direction of the central axis C, the direction along which slit 4X extends may be inclined from the direction of the central axis C. In this case, since it is difficult to form the slit 4X inclined with respect to the cylindrical shaped sensor head 4, the configuration of the above embodiments is preferable.

Further, the sensor head 4 may be formed in a tubular shape having a rectangular shape in cross section or polygonal shape in cross section other than the cylindrical shape.

In the second embodiment, although the light absorbing portions 15 (light absorbing members 15a to 15c) are provided between the respective two of the light source 5, transmitted light detector 6, and scattered light detector 7, the light absorbing portion 15 may be provided in at least one of them. In this case, it is preferable that the light absorbing portion 15 is provided between the light source 5 and the scattered light detector 7 which is installed close to the light source.

In addition, it is needless to say that various changes and combinations of the embodiments may be performed without being against the spirit of the present invention.

REFERENCE CHARACTER LIST

100 . . . Turbidimeter
Sa . . . Measurement space
L1 . . . inspection light
L2 . . . Transmitted light
L3 . . . Scattered light
C . . . Central axis
4 . . . Sensor head
41 . . . Bottom wall.
42 . . . Side wall
4X . . . Slit
Sb1 . . . Light source accommodating space
Sb2 . . . Transmitted light detector accommodating space
Sb3 . . . Scattered light detector accommodating space
M1 . . . Inspection light optical window
M2 . . . Transmitted light optical window
M3 . . . Scattered light optical window
5 . . . Light source
6 . . . Transmitted light detector
7 . . . Scattered light detector
8 . . . Housing for accommodating arithmetic equipment and the like
9 . . . Holding member
10 . . . Cleaning mechanism
11 . . . Cleaning unit
12 . . . Rotating unit
12a . . . Inspection light, passage hole
12b . . . Transmitted light passage hole
12c . . . Scattered light passage hole
12d . . . Anti-reflective passage hole
12H . . . Through-hole

The invention claimed is:

1. A turbidimeter comprising:
a closed-bottom cylindrical sensor head forming a measurement space in which a sample is accommodated without a vessel;
a light source for irradiating inspection light to the measurement space;
a transmitted light detector for detecting transmitted light passing through the measurement space; and
a scattered light detector for detecting scattered light scattered in the measurement space, wherein
the sensor head is formed of a material having optical transparency,
a side wall of the sensor head comprises an inner surface and an outer surface separated by a wall thickness, and a plurality of accommodating spaces formed within the wall thickness which accommodate the light source, transmitted light detector, and scattered light detector, respectively optically transparent portions of the inner surface of the side wall adjacent the plurality of accommodating spaces of the sensor head are configured to serve as: an inspection light optical window for guiding the inspection light to the measurement space; a transmitted light optical window for guiding the transmitted light to the transmitted light detector; and a scattered light optical window for guiding the scattered light to the scattered light detector, and
each of the optical windows, the inner surface of the side wall which forms the accommodating spaces, and the outer surface of the side wall which forms the plurality of accommodating spaces are formed integrally together of the material having the optical transparency such that the side wall has the optical transparency throughout its wall thickness for at least a portion of the side wall.

2. The turbidimeter according to claim 1, wherein, in the side wall of the sensor head, a light absorbing portion is provided between any two of the light source, the transmitted light detector, and the scattered light detector.

3. The turbidimeter according to claim 2, wherein the light absorbing portion is exposed on the inner surface of the side wall of the sensor head.

4. The turbidimeter according to claim 2, wherein the light absorbing portion is formed by embedding a light absorbing member in the side wall of the sensor head, and a thickness of the light absorbing member in a radial direction of the sensor head is smaller than a thickness of the side wall of the sensor head.

5. The turbidimeter according to claim 1, wherein the accommodating spaces are formed for respectively corresponding to the light source, transmitted light detector, and scattered light detector, and each of the accommodating spaces is formed along a central axis direction from a bottom wall side in the side wall of the sensor head.

6. The turbidimeter according to claim 1, wherein a through-hole is formed in the side wall of the sensor head at a position different from the accommodating spaces.

7. The turbidimeter according to claim 1 further comprising a cleaning unit for cleaning the inspection light optical window, transmitted light optical window, and scattered light optical window.

8. The turbidimeter according to claim 1, wherein the inner surface of the side wall of the sensor head is formed to have a cylindrical shape, and
the cleaning unit is configured to be rotated about the central axis of the inner surface of the side wall and has a contacting portion contacting over a predetermined range in the central axis direction of the inner surface of the side wall.

9. The turbidimeter according to claim 8, wherein the sensor head has a slit formed along the central axis direction for communicating the inner surface and outer surface of the side wall of the sensor head, having a configuration so that dust collected by the cleaning unit is discharged from the slit to the outside with rotation of the cleaning unit.

10. The turbidimeter according to claim 1 further comprising a single holding member for holding the light source, transmitted light detector, and scattered light detector, wherein the light source, transmitted light detector, and scattered light detector are accommodated in the accommodating spaces by attaching the holding member to the sensor head.

* * * * *